United States Patent [19]

Umemoto et al.

[11] Patent Number: 5,066,795
[45] Date of Patent: Nov. 19, 1991

[54] PERFLUOROALKYL-CONTAINING COMPOUND

[75] Inventors: Teruo Umemoto; Sumi Ishihara, both of Sagamihara, Japan

[73] Assignee: Sagami Chemical Research Center, Tokyo, Japan

[21] Appl. No.: 476,542

[22] Filed: Feb. 7, 1990

[30] Foreign Application Priority Data

Feb. 10, 1989 [JP] Japan .................................. 1-29705
Apr. 18, 1989 [JP] Japan .................................. 1-96325

[51] Int. Cl.$^5$ .................. C07D 329/00; C07D 345/00;
C07D 333/76; C07D 327/04
[52] U.S. Cl. .......................................... 540/1; 549/16;
549/43
[58] Field of Search ................. 540/1; 549/16, 43, 48,
549/388, 394

*Primary Examiner*—Robert Gerstl
*Attorney, Agent, or Firm*—Wenderoth, Lind & Ponack

[57] ABSTRACT

A (perfluoroalkyl)dibenzonium salt represented by the following general formula

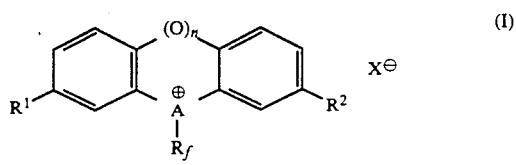

wherein $R_f$ represents a perfluoroalkyl group having 1 to 10 carbon atoms, A represents a sulfur of selenium atom, $R^1$ and $R^2$, independently from each other, represent a hydrogen atom or a nitro group, $X^\ominus$ represents a conjugated base of Brönsted acid, and n is 0 or 1.

The said compound is useful as a reagent for introducing a perfluoroalkyl group.

6 Claims, No Drawings

PERFLUOROALKYL-CONTAINING COMPOUND

This invention relates to novel perfluoroalkylcontaining compounds, and more specifically, to (perfluoroalkyl)dibenzonium salts represented by the following general formula

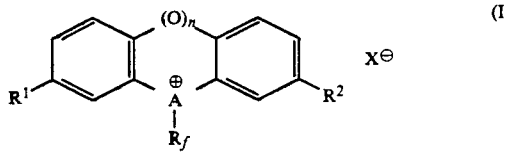

wherein $R_f$ represents a perfluoroalkyl group having 1 to 10 carbon atoms, A represents a sulfur or selenium atom, $R^1$ and $R^2$, independently from each other, represent a hydrogen atom or a nitro group, $X^\ominus$ represents a conjugated base of Brönsted acid, and n is 0 or 1, and novel intermediate compounds useful for the production of the aforesaid compounds.

The (perfluoroalkyl)dibenzonium salts of general formula (I) are useful as reagents for introducing perfluoroalkyl groups into various organic compounds (to be referred to as "perfluoroalkyl introducing reagents"), particularly as reagents for introducing perfluoroalkyl groups into a carbanion (see Referential Examples given hereinbelow).

For example, the use of the (perfluoroalkyl)dibenzonium salts can easily synthesize dialkyl methyl(trifluoromethyl)malonates in one step from carbonions of dialkyl methylmalonates which are easily available (see Referential Examples 1 to 3, 7, 9 and 10).

Previously, dialkyl methyl(trifluoromethyl)malonate has been produced by starting from perfluoroisobutylene, preparing a dialkyl (trifluoromethyl) -malonate through several steps of reaction, and reacting it further with methyl iodide in the presence of an excess of cesium fluoride [see Bull. Chem. Soc. Jpn., 56, 724 (1983)]. However, since this method requires several reaction steps and the starting perfluoroisobutylene is a highly toxic compound ($LD_{50}$: 0.5 ppm v/v) [see Chemiker-Zeitung, 100, Jahrgang (1976) Nr. 1, pp. 3–14], it cannot be a useful synthesis method.

On the other hand, 4-chlorophenyl-2',4'-dimethylphenyl(trifluoromethyl)sulfonium hexafluoroantimonate and 4-chlorophenyl-4'-methoxyphenyl(trifluoromethyl)sulfonium hexafluoroantimonate were proposed as reagents for introducing a trifluoromethyl group [see J. Org. Chem. USSR, 20, 103 (1984)]. However, since the production processes for these compounds are long and require the use as one starting material $SF_3^{\oplus}SbF_6^{\ominus}$ (see J. Chem. Soc., 1961, 3417) produced by using an excess of $SF_4$ having strong toxicity, these processes are not industrially advantageous. From the standpoint of the trifluoromethyl group introducing reagent, only the trifluoromethylation reaction of a p-nitrothiophenoxide ion has so far been reported.

A (perfluoroalkyl)phenyliodonium salt [see Bull. Chem. Soc. Jpn., 59, 439 (1986)] known as a reagent for perfluoroalkylation of carbanions have the defect that when they are used for perfluoroalkylation of carbanions such as 1,3-diketones and β-keto esters, mixtures of two isomers are obtained and their yields are low. It was reported J. Org. Chem., 48, 347 (1983)] that a perfluoroalkyl iodide becomes a good perfluoroalkylating agent for a carbanion of 2-nitropropane, but it has the serious defect that it cannot be a perfluoroalkyl group introducing reagent for carbanions of malonic acid diesters [J. Org. Chem., 50, 3269 (1985)].

A method of trifluoromethylating 1,3-diketone or the like by electrolytic reaction using trifluoroacetic acid was also reported Chem. Lett. 1988, 853]. But by-products are prone to occur because of the low reaction selectivity. Furthermore, the reaction conditions are limited because the reaction is an electrolytic reaction, and the applicability of the reaction is narrow.

The present inventors extensively worked in order to solve the above problems of the prior art. These investigations have now led to the discovery of the (perfluoroalkyl)dibenzonium salts of general formula (I) which are novel compounds and can induce perfluoroalkylation of various organic compounds with good efficiency.

The "perfluoroalkyl group" denotes a group resulting from replacing all hydrogen atoms bonded to the carbon atoms of the alkyl group with fluorine atoms. The alkyl group may be of straight chain or branched chain. Specific examples of the "perfluoroalkyl group having 1 to 10 carbon atoms' include trifluoromethyl, perfluoroethyl, n-perfluoropropyl, perfluoroisopropyl, n-perfluorobutyl, sec-perfluorobutyl, tert-perfluorobutyl, n-perfluoropentyl, n-perfluorohexyl, perfluorooctyl, perfluorononyl and perfluorodecyl groups.

The conjugated base of Brönsted is defined as follows by the theory of acid and base.

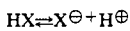

As shown by the above formula, a substance HX which acts as a proton ($H^\oplus$) donor is called Brönsted acid. $X^\ominus$ resulting from a loss of $H^\oplus$ is called a conjugated base of the Brönsted acid HX. $X^\ominus$ in general formula (I) in this invention may be a conjugated base of Brönsted acid which is so-called a strong acid having an acid dissociation index pKa of not more than 1. Examples include trifluoromethanesulfonate anion, difluoromethanesulfonate anion, methanesulfonate anion, trichloromethanesulfonate anion, perfluoroethanesulfonate anion, tetrafluoroethanesulfonate anion, perfluorobutanesulfonate anion, benzenesulfonate anion, toluenesulfonate anion, hydrogen sulfate anion, fluorosulfonate anion, chlorosulfonate anion, chlorine anion $BF^\ominus$, $SbF_6^\ominus$, $SbCl_5F^\ominus$, $SbCl_6^\ominus$, $AsF_6^\ominus$, $BCl_4^\ominus$, $BCl_3F^{63}$, $AlCl_4^\ominus$, $AlCl_3F^\ominus$, and $PF_6^\ominus$.

Preferred compounds among the compounds of formula (I) provided by this invention are (i) compounds of formula (I) in which $R^1$ and $R^2$ represent hydrogen atoms;

(ii) compounds of formula (I) in which either one of $R^1$ and $R^2$, or both, represent a nitro group; and Symbol A in general formula (I) may represent a sulfur atom or a selenium atom, preferably the sulfur atom. Preferred examples of the conjugated base ($X^\ominus$) of Brönsted acid are $^\ominus BF_4$, $^\ominus OSO_2CF_3$, $^\ominus AsF_6$, $^\ominus SbF_6$, and $^\ominus OSO_2CH_3$.

The compound of general formula (I) in which both of $R^1$ and $R^2$ are hydrogen atoms, provided by this invention, can be produced, for example through the route shown by the following reaction scheme A.

Reaction Scheme A

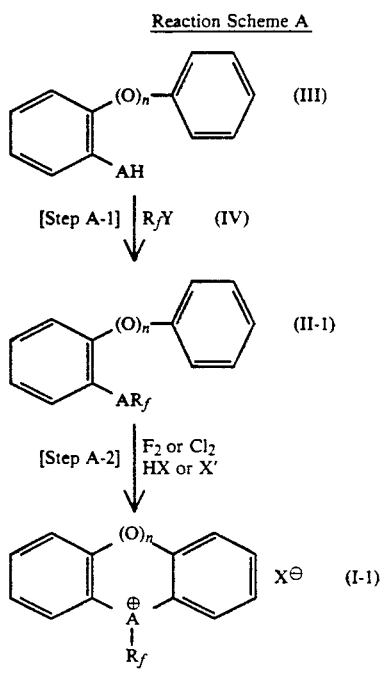

In the above reaction scheme, $R_f$, A and n are as defined above; Y represents an iodine or bromine atom; HX represents Brönsted acid; and X' represents a Lewis acid.

Each step of the process for producing unsubstituted (perfluoroalkyl)dibenzonium salts of formula (I-1) by the reaction scheme A will be described in detail.

[Step A-1]

In this step, a diphenyl compound of formula (III) is reacted with a perfluoroalkyl halide of formula (IV) under alkaline conditions under light irradiation or non-irradiation to produce a perfluoroalkyldiphenyl compound of formula (II-1).

The diphenyl compound of formula (III) used in this step is a known compound, or a compound which can be easily synthesized in the same way as in the production of a known diphenyl compound (see J. Org. Chem., 22, 561 (1957); J. Pharm. Soc. Japan, 72, 206 (19752); Chem. Ber. 72, 582 (1939); and Example 5 given hereinbelow].

The perfluoroalkyl halide of formula (IV) is an industrially obtainable compound, and may be, for example, a linear or branched perfluoroalkyl bromide or a perfluoroalkyl iodide. Specific examples include trifluoromethyl bromide, trifluoromethyl iodide, perfluoroethyl bromide, perfluoroethyl iodide, perfluoropropyl bromide, perfluoropropyl iodide, perfluorobutyl bromide, perfluorobutyl iodide, perfluoropentyl bromide, perfluoropentyl iodide, perfluorohexyl bromide, perfluorohexyl iodide, perfluorooctyl bromide, perfluorooctyl iodide, perfluorononyl bromide, perfluorononyl iodide, perfluorodecyl bromide, and perfluorodecyl iodide.

Examples of the alkalies used in this invention include alkali metal hydroxides such as sodium hydroxide and potassium hydroxide, alkali metal alkoxides such as sodium methoxdide, sodium ethoxide and potassium butoxide; alkali metal hydrides such as sodium hydride, potassium hydride and lithium hydride; ammonia; and organic amines such as ethylamine, diethylamine and triethylamine.

This step is usually carried out preferably in a solvent. Polar solvents such as diemthylformamide, dimethylacetamide, dimethyl sulfoxide, dimethylsulfone, tetramethylenesulfone, liquid ammonia, acetone, acetonitrile, methanol and ethanol are preferred as the solvent that can be used in this step. The reaction temperature is generally from about $-80°$ C. to about $+150°$ C. To perform the reaction in good yields, it is preferable to carry out the reaction at a temperature of $-60$ to $+100°$ C. If a perfluoroalkyl bromide is used as the perfluoroalkyl halide of formula (IV), it is preferred to perform the reaction in this step under light irradiation. The light source for irradition may be, for example, a light source generally used in photochemical reactions, for example, a low-pressure or high-pressure mercury lamp or a glow lamp which at least emits active light having a wavelength of 180 to 400 nm.

The amount of the perfluoroalkyl halide of formula (IV) relative to the diphenyl comound of formula (III) is not critical. Usually, it is 0.9 to 3 moles, especially 1 to 2 moles, per mole of the diphenyl compound (III). Conveniently, the alkali is used in an amount of 0.9 to 1.5 moles, preferably 1 to 1.2 moles, per mole of the compound of formula (III)

[Step A-2]

In this step, the perfluoroalkyldiphenyl compound of formula (II-1) obtained in step A-1 is reacted with the Brönsted acid (HX) or the Lewis acid (X') to produce the unsubstituted (perfluoroalkyl)dibenzonium salts of formula (I-1).

Preferably, in this step, the perfluoroalkyldiphenyl compound of formula (II-1) is usually reacted with fluorine or chlorine and then with the Brönsted acid (HX) or the Lewis acid (X').

The fluorine used in this step is preferably a fluorine gas usually diluted with 99 to 50% of an inert gas to inhibit its vigorous reaction. The diluting inert gas may be, for example, nitrogen, helium or argon. The amounts of fluorine and chlorine used cannot be generally determined because they may vary depending upon the method of introducing them, the reaction temperature, the reaction solvent and the reaction apparatus. Any one skilled in the art can easily determine them by performing routine experiments by taking the amounts of fluorine and chlorine required for substantial disappearance of the starting perfluoroalkyldiphenyl compound of formula (II-1) as a standard.

Examples of the Brönsted acid (HX) that can be used in this step are strong Brönsted acids such as trifluoromethanesulfonic acid, difluoromethnesulfonic acid, methanesulfonic acid, trichloromethanesulfonic acid, perfluoroethanesulfonic acid, tetrafluoroethanesulfonic acid, perfluorobutanesulfonic acid, benzenesulfonic acid, toluenesulfonic acid, sulfuric acid, fluorosulfonic acid, chlorosulfonic acid, hydrogen chloride, $HBF_4$, $HSbF_6$, $HSbCl_5F$, $HSbCl_6$, $HAsF_6$, $HBCl_4$, $HBCl_3F$, $HAlCl_4$, $HAlCl_3F$ and $HPF_6$.

Examples of the Lewis acid (X') that can be used in this step are strong Lewis acids such as $BF_3$, $SbF_5$, $SbCl_5$, $AsF_5$, $BCl_3$, $AlCl_3$ and $PF_5$.

The amount of the Brönsted acid or the Lewis acid is not critical. But to have this reaction proceed well, the amount of the Brönsted or Lewis acid is at least an equal molar ratio, economically a nearly equal proportion, to the perfluoroalkyldiphenyl compound of formula (II-1).

If the Brönsted or Lewis acid used in this reaction is liquid, it may be used in an excessive amount to make it serve concurrently as a solvent. In view of economy and the ease of after-treatment, it is preferred to use a halogen-containing organic solvent. Examples include trichlorofluromethane, trichlorotrifluoromethane, dichlorotrifluoromethane, methylene chloride, carbon tetrachloride, chloroform, trifluoroacetic acid and trifluoroacetic anhydride. The reaction temperature may be $-100$ to about $+40°$ C. when the perfluoroalkyldiphenyl compound of formula (II-1) is reacted with fluorine or chlorine. Temperatures of $-85$ to $+20°$ C. are preferred to obtain good yields and selectivities. When it is reacted with the Brönsted acid (HX) or the Lewis acid (X'), the reaction temperature may be about $-100$ to about $+100°$ C. The preferred temperature may be $-85$ to $+60°$ C. to perform the reaction in good yields.

The unsubstituted (perfluoroalkyl)dibenzoonium salts of formula (I-1) so obtained may be isolated and purified by known methods such as crystallization and chromatography.

Compounds of general formula (I-1) provided in this invention in which the conjugated base $(X^{\ominus})$ of Brönsted acid is $R_fSO_3^{\ominus}$ and $R_f'$ represents a lower perfluoroalkyl group may be produced also by the route shown in the following reaction scheme B.

Reaction Scheme B

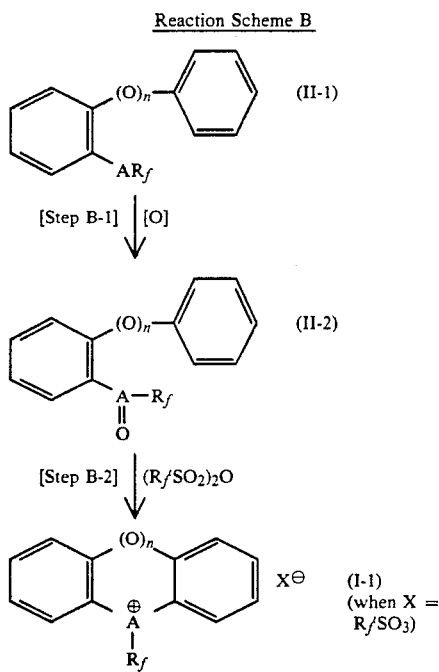

In the reaction scheme B, $R_f$, A and n are as defined above; $R_f'$ represents a lower perfluoroalkyl group.

Each of the steps of the process for production of the compound of formula (I-1) shown in the reaction scheme B (wherein x represents a lower perfluoroalkanesulfonyloxy group) will be described further in detail.

[Step B-1]

In this step, the perfluoroalkyldiphenyl compound of formula (II-1) obtained as an intermediate by the process shown in the reaction scheme A is treated with an oxidizing agent to produce a perfluoroalkyloxo compound of formula (II-2).

Examples of the oxidizing agent used in this step include hydrogen peroxide, peracetic acid, trifluoroperacetic acid, perbenzoic acid, m-chloroperbenzoic acid, potassium permanganate, sodium periodate and ozone. The amount of the oxidizing agent used is preferably at least 0.7 equivalent but not more than 1.5 equivalents, especially 0.8 to 1.3 equivalents in order to have this reaction proceed selectively.

Preferably, the reaction is generally carried out in a solvent. The solvent may be, for example, a halogenated hydrocarbon such as methylene chloride and chloroform. The reaction temperature may usually be about $-50$ to about $+100°$ C. For the reaction to proceed in good yields, the reaction temperature is preferably from $-30$ to $+50°$ C.

[Step B-2]

In this step, the perfluoroalkyloxo compound of formula (II-2) obtained in step B-1 is reacted with a lower perfluoroalkanesulfonic anhydride of formula (V) to produce the unsubstituted (perfluoroalkyl)dibenzonium salts of formula (I-1) in which X is $R_fSO_3$.

The lower perfluoroalkanesulfonic anhydride used in this reaction may be, for example, trifluoromethanesulfonic anhydride, and is an easily available compound. The amount of the lower perfluoroalkanesulfonic anhydride used is at least an equimolar proportion relative to the compound of formula (II-2) to have the reaction proceed in good yields. But from an economical standpoint, it is preferably a nearly equimolar proportion. Preferably, this reaction is usually carried out in a solvent. The solvent used may be, for example, trichlorofluoromethane, dichlorotrifluoroethane, trichlorotrifluoroethane, chlorotrifluoroethane, methylene chloride, carbon tetrachloride, chloroform, trifluoroacetic acid, trifluoroacetic anhydride, or trifluoromethanesulfonic acid. The reaction temperature is usually about $-20$ to $+100°$ C. To have the reaction proceed in good yields, the reaction temperature is preferably 0 to $70°$ C.

The compound of formula (I-1) in which X is $R_fSO_3$ may be isolated and purified by known methods such as crystallization and chromatography.

The compounds of formulae (II-1) and (II-2) obtained as intermediates in the reaction schemes A and B, namely (perfluoroalkyl)arylhetero compounds of the following general formula

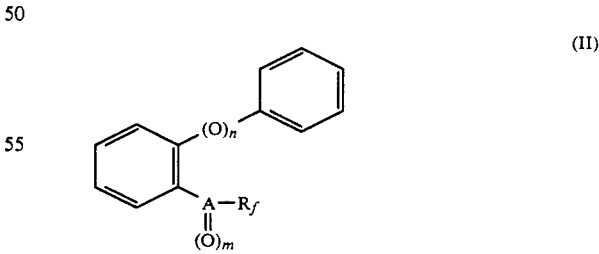

wherein $R_f$, A and n are as defined above and m is 0 or 1, are novel compounds not described in the literature, and also constitute one subject matter of this invention.

As shown in the following reaction scheme C, compounds of general formula (I), in which one or both of $R^1$ and $R^2$ are nitro groups, can be produced by electrophilic nitration of unsubstituted (perfluoroalkyl)dibenzonium salts (I-1) obtained by processes shown in reaction schems A and B.

Reaction Scheme C

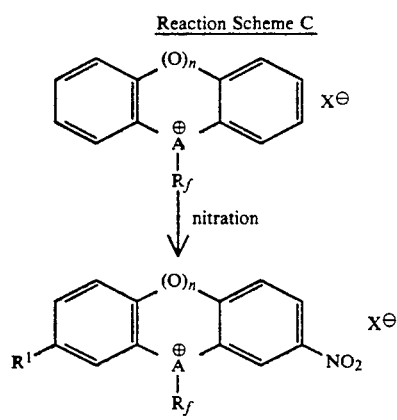

wherein $R_f$, A, $X^\ominus$, $R^1$ and n are as defined above.

The nitration does not necessarily require the use of a solvent. However, to have the reaction proceed efficiently, the reactions are preferably carried out in a solvent such as acetonitrile, nitromethane, tetramethylenesulfone, trifluoromethanesulfonic acid or trifluoroacetic acid. For example, nitronium trifluoromethanesulfonate, nitronium tetrafluoroborate and nitronium hexafluorophosphate may be used as the reagents for nitration. The amount of these reagents used may be varied according to the number of nitro group to be introduced. For example, when one nitro group is to be introduced, the reagent may preferably be used in an amount of 1 to 1.5 equivalents per mole of the compound of formula (I-1). When two nitro groups are to be introduced, the reagent is preferably used in an amount of 2 to 4 equivalents per mole of the compound of formula (I-1).

The temperature for the nitration depends upon the reactivity of the reagent used and the reactivity of the starting compound of formula (I-1), but the suitable temperature is generally about $-20$ to about $+100°$ C.

The nitrated (perfluoroalkyl)dibenzonium salts of formula (I-2) so obtained may be isolated and purified by known methods such as crytallization.

The (perfluoroalkyl)dibenzonium salts of general formula (I) are useful as perfluoroalkyl introducing reagents for introduction of perfluoroalkyl groups into various organic compounds. The perfluoroalkylation reaction can be easily carried out by mixing an organic compound into which the perfluoroalkyl group is desired to be introduced with the compound of formula (I) of the invention in an ordinary glass vessel using a solvent such as dimethylformamide or tetrahydrofuran (see Referential Examples 1 to 18 given hereinafter).

Examples of the organic compounds into which the perfluoroalkyl group can be introduced by the above method are metal salts of active methylene compounds, metal acetylides, silyl enol ethers, enamines, active aromatic compounds and metal salts of thiol.

The following Examples and Referential Examples illustrate the present invention more specifically.

EXAMPLE 1

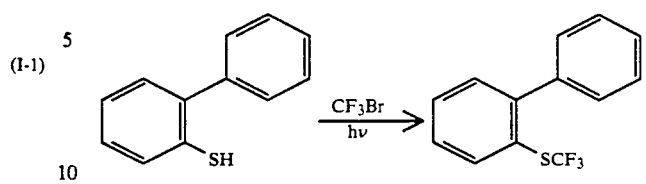

A reaction tube in a photoreaction apparatus was charged with 50 ml of dimethylformamide (DMF) and 5.59 g (30 mmol) of 2-mercaptobiphenyl, and with ice cooling and stirring, 1.2 g (30 mmol) of sodium hydride (60% in oil) was added. When foaming ceased, trifluoromethyl bromide was introduced into the reaction solution. The atmosphere within the reaction system was replaced by gaseous trifluoromethyl bromide, and while irradiating light from a high-pressure mercury lamp, about 2 equivalents of trifluoromethyl bromide was passed into the reaction system over about 2 hours. Ice water (150 ml) was added to the resulting brown reaction solution, and it was extracted with pentane. The organic layer was washed with water and then with saturated aqueous sodium chloride solution, and then dried over anhydrous magnesium sulfate. The anhydrous magnesium sulfate was removed by filtration, and the filtrate was concentrated under reduced pressure to give 6.71 g (87.9%) of 2-(trifluoromethylthio)biphenyl as an oil. It was purified by silica gel column chromatography. The properties of the product were as shown below.

$^{19}$F-NMR (in deuterochloroform, internal standard CCl$_3$F): 42.53 ppm (s). $^1$H-NMR (in deuterochloroform): 7.20-7.60 ppm (m, 8H), 7.78 ppm (br.d, J=7.5 Hz, 1H).

IR (neat): 3070, 1465, 1130, 1105, 755, 700 cm$^{-1}$.

Mass (m/e): 254 (M$^+$), 185 (M$^+$-CF$_3$), 69.

Elemental analysis: Found: C, 61.37; H, 3.65%. Calculated: C, 61.41; H, 3.57%.

EXAMPLE 2

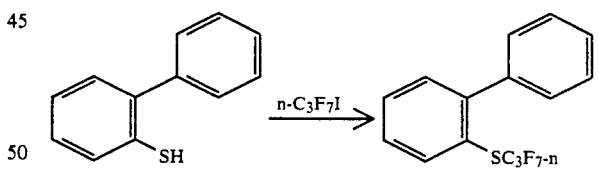

To a solution composed of 20 ml of DMF and 2.24 g (12 mmol) of 2-mercaptobiphenyl was added 481 mg (12 mmol) of sodium hydride (60% in oil) little by little under ice cooling and stirring. Then, 1.73 ml (12 mmol) of perfluoropropyl iodide was added dropwise. The temperature of the mixture was slowly elevated to room temperature, and the mixture was stirred for 2 days. The white precipitate formed in the reaction solution was removed by filtration. Water was addd to the filtrate, and the mixture was extracted with hexane. The organic layer was washed with water, dried over anhydrous magnesium sulfate, and filtered. The filtrate was concentrated under reduced pressure to give a brown oil. It was purified by silica gel column chromatography (ethyl acetate:hexane=1:30) to give 3.46 g (87.3%) of 2-(heptafluoropropylthio)biphenyl as a colorless oil. The properties of the product were as shown below.

19F-NMR (in deuterochloroform, internal standard CCl3F): 81.68 ppm (t, J=8.1 Hz, 3F), 87.75 ppm (m), 124.9 ppm (t, J=3.5 Hz, 2F).

1H-NMR (in deuterochloroform): 7.18–7.87 ppm (m).

IR (neat): 3075, 1465, 1335, 1210-1230, 1205, 1110, 915, 850, 750, 700 cm$^{-1}$.

Mass (m/e): 354 (M+), 185 (M+ −C3F7), 184, 69.

Elemental analysis: Found: C, 50.96; H, 2.58%. Calculated: C, 50.85; H, 2.56%.

EXAMPLE 3

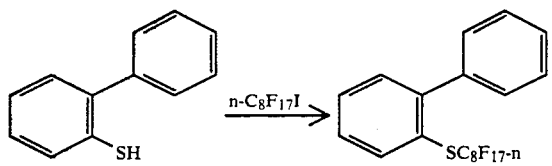

To a solution composed of 40 ml of DMF and 4.66 g (25 mmol) of 2-mercaptobiphenyl was added 1.00 g (25 mmol) of sodium hydride (60% in oil) little by little under ice cooling and stirring. Then, 13.6 g (25 mmol) of perfluorooctyl iodide was added. The temperature of the mixture was slowly elevated to room temperature, and the mixture was stirred for 2 hours. Water was addd to the reaction mixture, and the mixture was extracted with hexane. The organic layer was washed with saturated aqueous sodium chloride solution, dried over anhydrous magnesium sulfate, and filtered. The filtrate was concentrated under reduced pressure to give a brown oil. It was purified by silica gel column chromatography using hexane as an eluent to give 9.60 g (64%) of 2-(perfluorooctylthio)biphenyl as a colorless oil. The properties of the product were as shown below.

19F-NMR (in deuterochloroform, internal standard CCl3F): 81.4 ppm (t, J=9.0 Hz, 3F), 86.1 ppm (m, 2F), 119.3 ppm (m, 2F), 121.4 ppm (m, 8F), 126.0 ppm (m, 2F).

1H-NMR (in deuterochloroform): 7.17–7.59 ppm (m, 8H), 7.79 ppm (br.d, J=6.0 Hz, 1H).

IR (neat) 1205, 1045, 955, 755, 700 cm$^{-1}$.

Mass (m/e): 604 (M+), 185 (M+ −C8F17), 119, 69.

Elemental analysis: Found: C, 39.51; H, 1.49%. Calculated: C, 39.75; H, 1.50%.

EXAMPLE 4

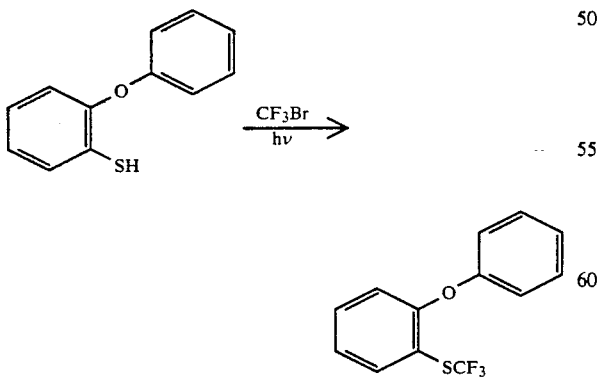

Example 1 was repeated except that 1-mercapto-2-phenoxybenzene was used instead of 2-mercaptobiphenyl. As a result, 1.03 g (84.7%) of 2-phenoxy-1-trifluoromethylthiobenzene was obtained as a yellow oil.

19F-NMR (in deuterochloroform, internal standard CCl3F): 42.0 ppm (s).

1H-NMR (in deuterochloroform): 6.77–7.75 ppm (m).

EXAMPLE 5

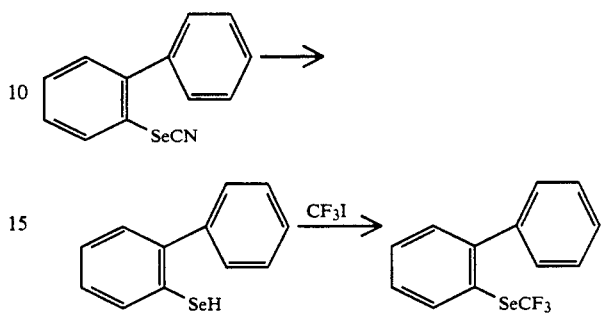

A solution composed of 30 ml of DMF and 5.16 g (20 mmol) of 2-selenocyanatobiphenyl was cooled to −30° C., and trifluoromethyl iodide was introduced into the cooled solution. The atmosphere in the reaction system was replaced by gaseous trifluoromethyl iodide. With stirring at −30° C., 915 mg (24 mmol) of sodium borohydride was added to perform reduction and to give a sodium salt of biphenyl-2-selenol. While passing trifluoromethyl iodide into the reaction system, the temperature was slowly elevated to 0° C. Water (80 ml) was added to the reaction solution, and the mixture was extracted with hexane. The organic layer was washed with water and saturated aqueous sodium chloride solution, and then dried over anhydrous sodium sulfate. The anhydrous sodium sulfate was removed by filtration, and the filtrate was concentrated under reduced pressure. The resulting brown oil was purified by silica gel column chromatography (ethyl acetate:hexane=1:20) to give 4.05 g (67.3%) of 2-(trifluoromethylseleno)biphenyl as white crystals. The properties of the product were as shown below.

Melting point: 44–45° C.

19F-NMR (in deuterochloroform, internal standard CCl3F): 36.0 ppm (s).

1H-NMR (in deuterochloroform): 7.17–7.52 ppm (m, 8H), 7.87 ppm (br.d, J=6 Hz, 1H).

IR (KBr-Disk): 3060, 1460, 1445, 1130, 1095, 750, 700 cm$^{-1}$.

Elemental analysis: Found: C, 51.85; H, 3.09%. Calculated: C, 51.85; H, 3.01%.

EXAMPLE 6

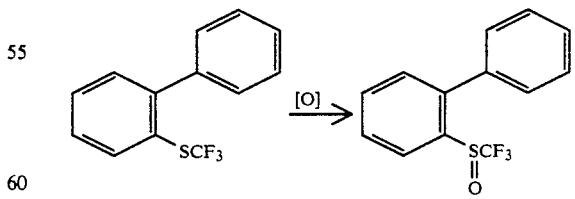

Under ice cooling, 7.77g (31.5 mmol) of m-chloroperbenzoic acid was added little by little to a solution of 7.63 g (30 mmol) of 2-(trifluoromethylthio)biphenyl in 20 ml of methylene chloride with stirring. The mixture was stirred overnight at room temperature. The precipitate in the reaction mixture was removed by filtration, and the filtrate was concentrated under reduced pressure. The residue was purified by silica gel column chromatography (ethyl acetate:hexane=1:10) to give 7.93 g (97.8%) of 2-(trifluoromethylsulfinyl)biphenyl. The properties of the product were as shown below.

Melting point: 57-58° C.

$^{19}$F-NMR (in deuterochloroform, internal standard CCl$_3$F): 73.13 ppm (s).

$^1$H-NMR (in deuterochloroform): 7.21-7.48 ppm (m, 5H), 7.51-7.65 ppm (m, 3H), 8.18-8.28 ppm (m, 1H).

IR (neat): 3070, 1470, 1190, 1180, 1135, 1080, 750, 700 cm$^{-1}$.

Mass (m/e): 270 (M+), 201 (M+−CF$_2$).

Elemental analysis: Found: C, 57.72; H, 3.50%. Calculated: C, 57.77; H, 3.36%.

EXAMPLE 7

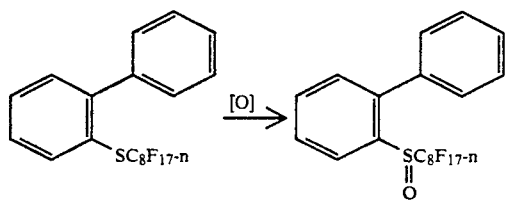

Under ice cooling, 3.57g (14.5 mmol) of m-chloroperbenzoic acid was added little by little to a solution of 8.76 g (14.5 mmol) of 2-(perfluorooctylthio)biphenyl in 50 ml of methylene chloride with stirring. The mixture was stirred overnight at room temperature. The precipitate in the reaction mixture was removed by filtration, and the filtrate was concentrated under reduced pressure. The residue was purified by silica gel column chromatography using hexane as an eluent to give 8.97 g (100%) of 2-(perfluorooctylsulfinyl)biphenyl as while crystals. The properties of the product were as shown below.

Melting point: 62-63° C.

$^{19}$F-NMR (in deuterochloroform, internal standard CCl$_3$F): 82.1 ppm (m, 3F), 122.6 ppm (m, 12F), 126.9 ppm (m, 2F).

$^1$H-NMR (in deuterochloroform): 7.23-7.71 ppm (m, 8H), 8.16-8.29 ppm (m, 1H).

IR (KBr-Disk): 1205, 1150, 1090, 920, 760, 705, 640 cm$^{-1}$.

Mass (m/e): 621 (M++1), 601 (M+−F), 201 (M+−C$_8$F$_{17}$), 69.

Elemental analysis: Found: C, 38.54; H, 1.27%. Calculated: C, 38.73; H, 1.46%.

EXAMPLE 8

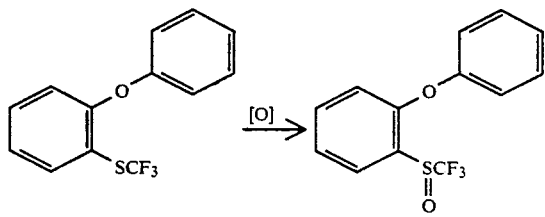

Example 5 was repeated except that 946 mg (3.5 mmol) of 2-phenoxy-1-trifluoromethylthiobenzene was used instead of 2-(trifluoromethylthio)biphenyl. As a result, 523 mg (52.2%) of 1-phenoxy-2-trifluoromethylsulfinylbenzene was obtained as pale yellow crystals.

$^{19}$F-NMR (in deuterochloroform, internal standard CCl$_3$F): 73.88 ppm (s).

$^1$H-NMR (in deuterochloroform): 6.77-8.18 ppm (m).

EXAMPLE 9

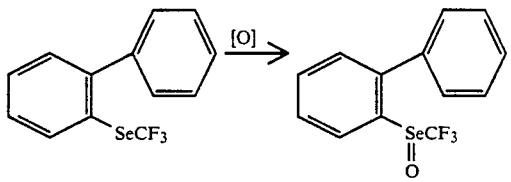

With stirring at −35° C., 518 mg (2.1 mmol) of m-chloroperbenzoic acid was added to a solution of 602 mg (2 mmol) of 2-trifluoromethylseleno)biphenyl in 5 ml of methylene chloride. The mixture was stirred for 30 minutes at −30° C. to −20° C. The precipitate in the reaction mixture was removed by filtration, and the filtrate was concentrated under reduced pressure The residue was purified by silica gel column chromatography (ethyl acetate:hexane=1:3) to give 610 mg (96.2%) of 2-(trifluoromethylseleninyl)biphenyl.

The properties of the product were as follows: Melting point: 157-152° C.

$^{19}$F-NMR (in deuterochloroform, internal standard CCl$_3$F): 63.0 ppm (s).

$^1$H-NMR (in deuterochloroform): 7.25-7.75 ppm (m, 8H), 8.23-8.34 ppm (m, 1H).

IR (KBr-Disk): 3080, 1470, 1060, 1100, 830, 755, 705 cm$^{-1}$.

Elemental analysis: Found: C, 49.12; H, 2.91%. Calculated: C, 49.23; H, 2.86%.

EXAMPLE 10

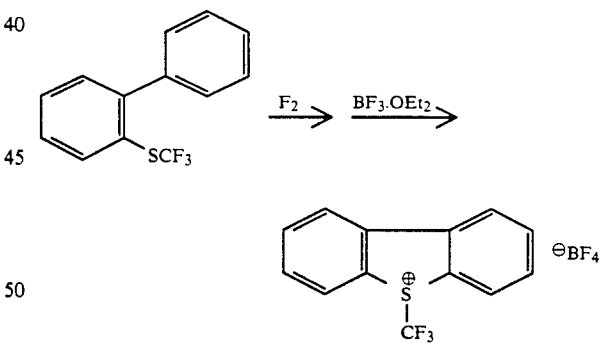

A gaseous mixture of fluorine and nitrogen (1:10) was introduced at a rate of 50 ml per minute into a solution of 2.54 g (10 mmol) of 2-(trifluoromethylthio)biphenyl in 20 ml of trichlorofluoromethane while being vigorously stirred on a bath at −78° C. When 12 mmol of fluorine gas was introduced, the introduction was stopped. To remove the remaining fluorine gas, a suitable amount of nitrogen gas was passed, and 1.23 ml (10 mmol) of boron trifluoride-ether complex was added to the reaction solution maintained at −78° C. Then, the temperature was slowly elevated to room temperature. The resulting pale yellow crystals were collected to obtain 2.52 g (74.1%) of S-(trifluoromethyl)dibenzothiophenium tetrafluoroborate. The properties of the product are summarized in Table 1.

EXAMPLE 11

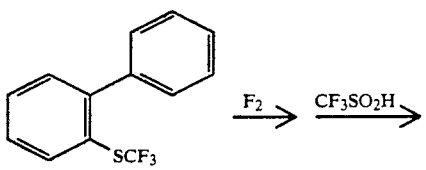

Example 10 was repeated except that trifluoromethanesulfonic acid was used instead of the boron trifluoride -ether complex. As a result, S-(trifluoromethyl)-dibenzothiophenium trifluoromethanesulfonate was obtained in a yield of 57%. The properties of the product are shown in Table 1.

EXAMPLE 12

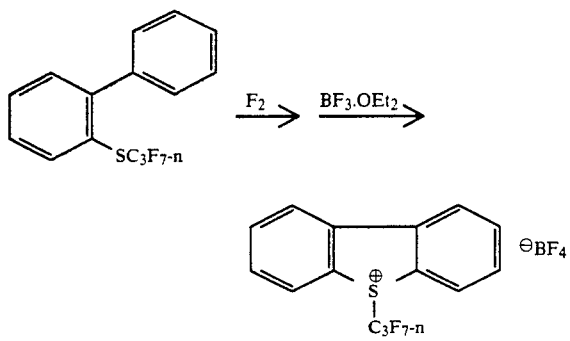

Example 10 was repeated except that 2-(heptafluoropropylthio)biphenyl was used instead of 2-(trifluoromethylthio)biphenyl. The reaction mixture was concentrated under reduced pressure. The residue was purified by silica gel thin-layer chromatography (acetonitrile:-methylene chloride=1:3) to give S-(heptafluoropropyl)dibenzothiophenium tetrafluoroborate as white crystals in a yield of 38.6%. The properties of the product are summarized in Table 1.

EXAMPLE 13

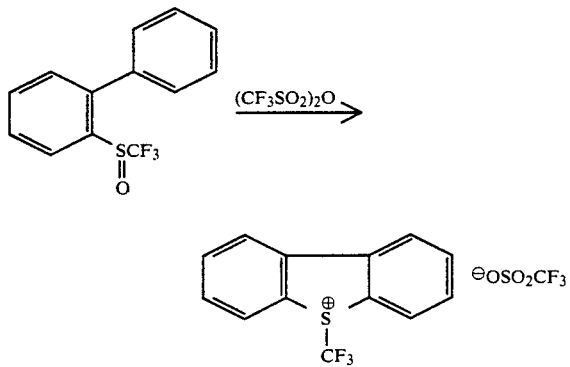

To a solution of 4.05 g (15 mmol) of 2-(trifluoromethylsulfinyl)biphenyl in 30 ml of 1,1,2-trichloro -1,2,2-trifluoroethane was added 2.52 ml (15 mmol) of trifluoromethanesulfonic anhydride, and the mixture was stirred at room temperature for 2 days. The white precipitate formed in the reaction system was collected by filtration to give 4.51 g (74.8%) of S-(trifluoromethyl)-dibenzothiophenium trifluoromethanesulfonate. The properties of the product are shown in Table 1.

EXAMPLE 14

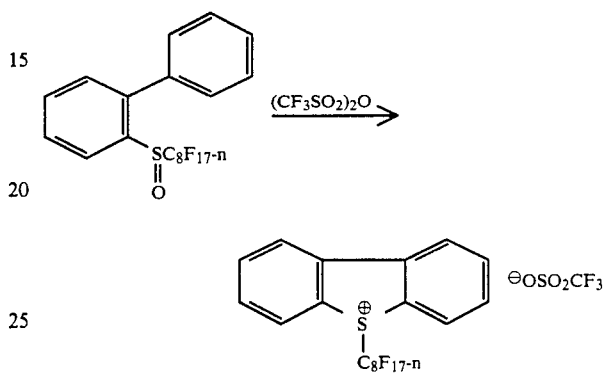

To a solution of 1.24 g (2 mmol) of 2-(perfluorooctylsulfinyl)biphenyl in 10 ml of 1,1,2-trichloro -1,2,2-trifluoroethane was added 0.336 ml (2 mmol) of trifluoromethanesulfonic anhydride, and the mixture was stirred at room temperature for 3 days. Then, 0.112 ml (0.67 mmol) of trifluoromethanesulfonic anhydride was added to the reaction mixture and the mixture was stirred for additional 2 days. After diethyl ether was added to the reaction mixture, a white precipitate was collected by filtration to give 1.36 g (91%) of S-(perfluorooctyl)dibenzothiophenium trifluoromethanesulfonate. The properties of the product are shown in Table 1.

EXAMPLE 15

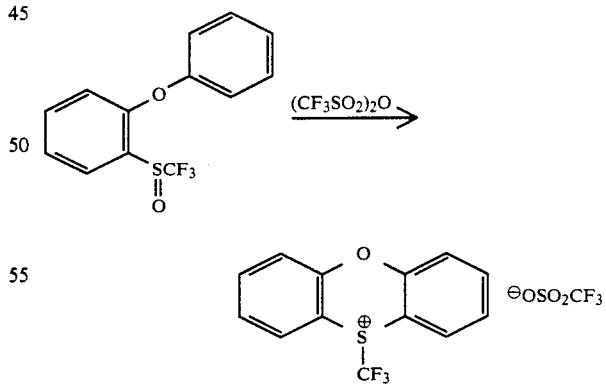

Trifluoromethanesulfonic anhydride 176 microliters (1.05 mmol) was added to a solution of 300 mg (1.05 mmol) of 1-phenoxy-2-(trifluoromethylsulfinyl)benzene in 8 ml of 1,1,2-trichloro-1,2,2-trifluoroetane, and the mixture was stirred for 6 days at room temperature. The reaction solution was concentrated under reduced pressure. The residue was purified by silica gel thin-layer chromatography (acetonitrile:methylene chloride=1:3)

to give 115 mg (26.2%) of S-(trifluoromethyl)dibenzo-1,4-oxathiinium trifluoromethanesulfonate as white crystals. The properties of the product are shown in Table 1.

EXAMPLE 16

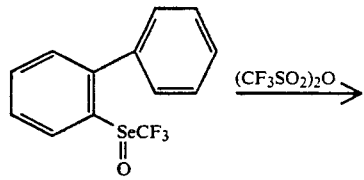

-continued

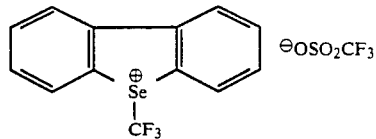

Under ice cooling, 3.71 ml (22 mmol) of trifluoromethanesulfonic anhydride was added to a solution of 6.99 g (22 mmol) of 2-(trifluoromethylseleninyl)biphenyl in 20 ml of methylene chloride. While the temperature was elevated to room temperature, the mixture was stirred for 2 hours. A white precipitate which formed when ether was added to the reaction solution was collected by filtration to give 9.33 g (94.4%) of Se(trifluoromethyl)dibenzoselenophenium trifluoromethanesulfonate.

The properties of the product are summarized in Table 1.

TABLE 1

| Example No. | Structural formula | Melting point (°C.) | ¹⁹F-NMR (ppm, CD₃CN, CFCl₃ internal standard) | ¹H-NMR (ppm, CD₃CN, TMS internal standard) | Mass (m/e) | Elemental analysis (calculated) C% | H% | S% | N% |
|---|---|---|---|---|---|---|---|---|---|
| 10 | dibenzothiophenium-CF₃ ⊖BF₄ | 171–172 (CH₃CN—Et₂O) | 52.5(3F, s) 150.1(4F, s) | 7.79–8.22(4H, m) 8.36–8.52(4H, m) | (SIMS method) 253(M⁺-BF₄) 184(253-CF₃) | — | — | 9.9 (9.4) | — |
| 11 13 | dibenzothiophenium-CF₃ ⊖OSO₂CF₃ | 155 (CH₃CN—Et₂O) | 52.9(3F, s) 78.0(3F, s) | 7.78–8.18(4H, m) 8.38–8.55(4H, m) | 184 (M⁺-OSO₂CF₃) 69(CF₃) | 41.75 (41.80) | 1.84 (2.00) | — | — |
| 12 | dibenzothiophenium-CF₂CF₂CF₃ ⊖BF₄ | 181 (AcOEt-Hexane) | 79.5(3F, t, J=8.8Hz) 93.4(2F, q, J=8.8Hz) 118.7(2F, s) 150.8(4F, s) | 7.78–8.27(4H, m) 8.37–8.48(4H, m) | (SIMS method) 353(M⁺+BF₄) 184(353-C₃F₇) | 40.67 (40.94) | 1.97 (1.83) | — | — |
| 14 | dibenzothiophenium-C₈F₁₇-n ⊖OSO₂CF₃ | 191–192 (with decomp.) (CH₃CN—Et₂O) | 78.0(3F, s) 79.8(3F, t, J=9.2Hz) 91.4(2F, m) 113.6(2F, m) 119.3–121.1(8F, m) 124.5(2F, m) | 7.75–8.18(4H, m) 8.30–8.41(4H, m) | 603(M⁺-OSO₂CF₃) 184(603-C₈F₁₇) | 33.40 (33.52) | 0.91 (1.07) | — | — |
| 15 | phenoxathiinium-CF₃ ⊖OSO₂CF₃ | 154 (AcOEt-Hexane) | 58.5(3F, s) 78.4(3F, s) | 7.51–8.33(m) | 269(M⁺-OSO₂CF₃) 200(269-CF₃) 69(CF₃) | 40.18 (40.20) | 2.09 (1.93) | — | — |
| 16 | dibenzoselenophenium-CF₃ ⊖OSO₂CF₃ | 170–172 (CH₃CN—Et₂O) | 45.5(3F, s) 78.2(3H, s) | 7.66–8.06(4H, m) 8.23–8.43(4H, m) | (SIMS method) 301(M⁺-OSO₂CF₃+1) 232(301-CF₃) | 37.33 (37.43) | 1.76 (1.79) | — | — |

TABLE 1-continued

| Example No. | Structural formula | Melting point (°C.) | $^{19}$F-NMR (ppm, CD$_3$CN, CFCl$_3$ internal standard) | $^1$H-NMR (ppm, CD$_3$CN, TMS internal standard) | Mass (m/e) | Elemental analysis (calculated) | | | |
|---|---|---|---|---|---|---|---|---|---|
| | | | | | | C % | H % | S % | N % |
| 17 | 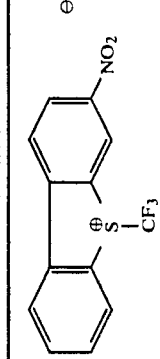 | 153 (CH$_3$CN—Et$_2$O) | 50.3(3F, s) 78.0(3F, s) | 7.84–8.28(2H, m), 8.44–8.64(4H, m) 8.86(1H, dd, J=9Hz, 1.5Hz) 9.28(1H, d, J=1.5Hz) | (SIMS method) 298(M$^+$-OSO$_2$CF$_3$) 229(298-CF$_3$) | 37.49 (37.59) | 1.48 (1.58) | — | 3.42 (3.13) |
| 18 | 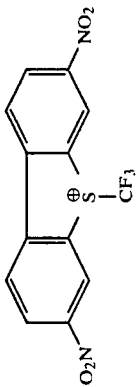 | 130–135 (with decomp.) (CH$_3$CN—Et$_2$O) | 48.8(3F, s) 78.4(3F, s) | 8.69(2H, d, J=9Hz) 8.91(2H, dd, J=9Hz, 1.8Hz) 9.34(2H, d, J=1.8Hz) | (SIMS method) 343(M$^+$-OSO$_2$CF$_3$) 274(343-CF$_3$) | — | — | — | — |
| 19 | 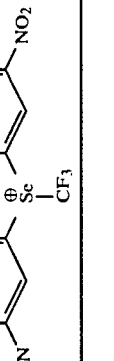 | 198–200 (with decomp.) (CH$_3$CN—Et$_2$O) | 42.0(3F, s) 78.2(3F, s) | 8.62(2H, d, J=9Hz) 8.83(2H, dd, J=9Hz, 2.1Hz) 9.27(2H, d, J=2.1Hz) | 391(M$^+$-OSO$_2$CF$_3$) 322(391-CF$_3$) | 31.26 (31.19) | 0.97 (1.12) | — | 5.17 (5.20) |

EXAMPLE 17

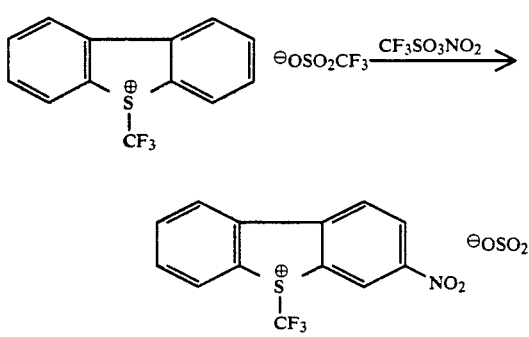

A mixture of 0.058 ml (1.3 mmol) of 94% nitric acid and 0.266 ml (1.58 mmol) of trifluoromethanesulfonic anhydride was stirred at room temperature for 1.5 hours to prepare nitronium trifluoromethanesulfonate, and then 2 ml of nitromethane and 502 mg (1 mmol) of S-(trifluoromethyl)dibenzothiophenium trifluoromethanesulfonate was added to the mixture. The reaction mixture was stirred overnight at room temperature and concentrated under reduced pressure. Diethyl ether was added to the residue and the resulting precipitate was collected by filtration to give 339 mg (76%) of 2-nitro-S-(trifluoromethyl)dibenzothiophenium trifluoromethanesulfonate as pale yellow crystals. The properties of the product are summarized in Table 1.

EXAMPLE 18

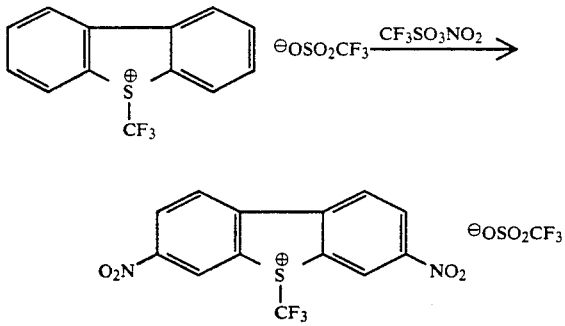

Trifluoromethanesulfonic anhydride 4.57 ml (27.2 mmol) was added to 0.94 ml (22.4 mmol) of 94% nitric acid and the mixture was stirred at room temperature for 1 hour to prepare nitronium trfluoromethanesulfonate. S-(trifluoromethyl)dibenzothiophenium trifluoromethanesulfonate 3.0 g (7.46 mmol) was added to the mixture and the reaction mixture was stirred for 2 day. Pale yellow crystals formed by addition of diethyl ether were collected by filtration and recrystallized from acetonitrile-diethyl ether to give 2.57 g (70%) of 2,7-dinitro-S-(trifluoromethyl)dibenzothiophenium trifluoromethanesulfonate. The properties of the product are summarized in Table 1.

EXAMPLE 19

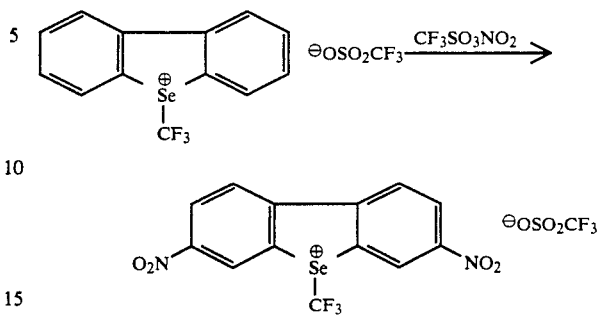

Example 18 was repeated except that 3.0 g (6.68 mmol) of Se-(trifluoromethyl)dibenzoselenophenium trifluoromethylsulfonate was used instead of S-(trifluoromethyl)dibenzothiophenium trifluoromethanesulfonate. As a result, 2.7 g (76%) of 2,7-dinitro-Se-(trifluoromethyl)dibenzoselenophenium trifluoromethanesulfonate was obtained as pale yellow crystals. The properties of the product are summarized in Table 1.

REFERENTIAL EXAMPLE 1

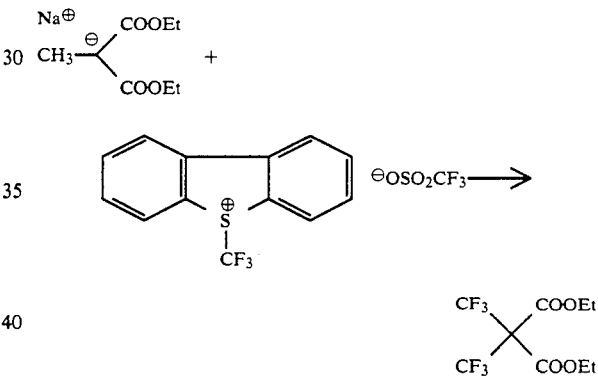

With ice cooling and stirring, 40 mg (1 mmol) of sodium hydride (60% in oil) was added little by little to a solution of 17.2 microliters (1 mmol) of diethyl methylmalonate. At −65° C., 402 mg (1 mmol) of S-(trifluoromethyl)dibenzothiophenium trifluoromethanesulfonate was added to the reaction solution. Then with stirring, the temperature was elevated to room temperature over about 5 hours. When the reaction solution was analyzed by $^{19}$F-NMR spectrum, it was found that diethyl methyl(trifluoromethyl)malonate was formed in a yield of 38%. The product was isolated in a conventional manner. Its spectral data are shown below.

$^{19}$F-NMR (in deuterochloroform, internal standard CCl$_3$F): 70.9 ppm (s).

$^1$H-NMR (in deuterochloroform): 1.27 (t, J=7 Hz, 6H), 1.67 (s, 3H), 4.27 ppm (q, J=7 Hz, 4H).

IR (neat) 1755 cm$^{-1}$ (ester).

Mass (m/e): 242 (M+), 197 (M+−EtO).

REFERENTIAL EXAMPLES 2-19

Perfluroalkyl compounds were produced by reacting various (perfluoroalkyl)dibenzonium salts with various compounds shown as substrates in Table 2. Table 2 also showed molar ratios of them, reaction solvents, reaction times, raction temperatures, and yields of the products.

The yields were determined by $^{19}$F-NMR except for that of Referential Example 19 which was based on the isolated product. With regard to the reaction operation, Referential Examples 2-12, 18 and 19 were done in a similar manner as Referential Example 1, and Referential Examples 13-16 were done as follows; the substrates were mixed with the (perfluoroalkyl)dibenzonium salts, the mixtures were stirred under the conditions shown in Table 2, and their post-treatment was done in a conventional manner. In Referential Example 17, the perfluoroalkylation was carried out in a similar manner as Referential Examples 13-16 and subsequent hydrolysis was done by adding concentrated hydrochloric acid and stirring overnight. The reactions of Referential Examples 13 and 14 were carried out in the presence of an equimolar pyridine, as a base, while that of Referential Example 17 in the presence of an equimolar 4-dimethylaminopyridines. The structures of the products were identified by analyzing their spectral data or by comparing with authentic samples.

TABLE 2

| Referential Example No. | Substrate | (I) | Molar ratio substrate/(I) | Solvent | Temperature | Time | Product | Yield (%) | ¹⁹F-NMR (ppm, CFCl₃, internal standard) |
|---|---|---|---|---|---|---|---|---|---|
| 2 | Na⊕ ⊖C(CH₃)(COOEt)₂ | Ph₂S⁺–CF₃ ⊖BF₄ | 1 | DMF | −65° C. → room temperature | overnight | CF₃–C(CH₃)(COOEt)₂ | 30 | 70.9(s) (in CDCl₃) |
| 3 | Na⊕ ⊖C(CH₃)(COOEt)₂ | (Ph–O–Ph)S⁺–CF₃ ⊖OSO₂CF₃ | 1 | DMF | −65° C. → room temperature | overnight | CF₃–C(CH₃)(COOEt)₂ | 28 | 70.9(s) (in CDCl₃) |
| 4 | 2-methyl-1,3-cyclopentanedione Na salt | Ph₂S⁺–CF₃ ⊖OSO₂CF₃ | 1 | DMF | −65° C. → room temperature | overnight | 2-methyl-2-trifluoromethyl-1,3-cyclopentanedione | 83 | 69.8(s) (in CDCl₃) |
| 5 | 2-methyl-1,3-cyclopentanedione Na salt | Ph₂S⁺–CF₃ ⊖BF₄ | 1 | DMF | −60° C. → room temperature | 5 hours | 2-methyl-2-trifluoromethyl-1,3-cyclopentanedione | 70 | 69.8(s) (in CDCl₃) |
| 6 | 2-methyl-1,3-cyclopentanedione Na salt | (Ph–O–Ph)S⁺–CF₃ ⊖OSO₂CF₃ | 1 | DMF | −65° C. → room temperature | overnight | 2-methyl-2-trifluoromethyl-1,3-cyclopentanedione | 69 | 69.8(s) (in CDCl₃) |

TABLE 2-continued

| Referential Example No. | Substrate | (I) | Molar ratio substrate/(I) | Solvent | Temperature | Time | Product | Yield (%) | $^{19}$F-NMR (ppm, CFCl$_3$, internal standard) |
|---|---|---|---|---|---|---|---|---|---|
| 7 | Na$^⊕$ CH$_3$–C$^⊖$(COOEt)(COOEt) CH$_3$ | dibenzoselenophenium-CF$_3$ $^⊖$OSO$_2$CF$_3$ | 1 | DMF | −65° C. → room temperature | 3 hours | CF$_3$–C(CH$_3$)(COOEt)(COOEt) | 26 | 70.9(s) (in CDCl$_3$) |
| 8 | 2-methyl-1,3-cyclopentanedione Na salt (CH$_3$) | dibenzoselenophenium-CF$_3$ $^⊖$OSO$_2$CF$_3$ | 1 | DMF | −65° C. → room temperature | 3 hours | 2-methyl-2-CF$_3$-1,3-cyclopentanedione | 74 | 69.8(s) (in CDCl$_3$) |
| 9 | Na$^⊕$ CH$_3$–C$^⊖$(COOEt)(COOEt) CH$_3$ | bis(4-nitrophenyl)sulfonium-CF$_3$ $^⊖$OSO$_2$CF$_3$ | 1 | DMF | −65° C. → room temperature | 1.5 hours | CF$_3$–C(CH$_3$)(COOEt)(COOEt) | 30 | 70.9(s) (in CDCl$_3$) |
| 10 | Na$^⊕$ CH$_3$–C$^⊖$(COOEt)(COOEt) CH$_3$ | bis(4-nitrophenyl)selenonium-CF$_3$ $^⊖$OSO$_2$CF$_3$ | 1 | DMF | −65° C. → room temperature | 2 hours | CF$_3$–C(CH$_3$)(COOEt)(COOEt) | 30 | 70.9(s) (in CDCl$_3$) |
| 11 | PhC≡C–Li$^⊕$ | dibenzothiophenium-CF$_3$ $^⊖$OSO$_2$CF$_3$ | 1.35 | THF | −78° C. → room temperature | overnight | PhC≡C–CF$_3$ | 30 | 49.7(s) (in THF) |

TABLE 2-continued
| Referential Example No. | Substrate | (I) | Molar ratio substrate/(I) | Solvent | Temperature | Time | Product | Yield (%) | 19F-NMR (ppm, CFCl3, internal standard) |
|---|---|---|---|---|---|---|---|---|---|
| 12 |  | 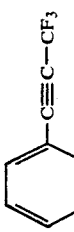 | 1.35 | THF | −78° C. ⟶ room temperature | overnight |  | 46 | 49.7(s) (in THF) |
| 13 |  | 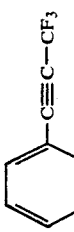 | 1 | DMF | 80° C. | overnight |  | 65 | 69.2(d, J=8.5Hz) (in CDCl3) |
| 14 |  | 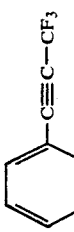 | 1 | DMF | 100° C. | overnight |  | 54 15 | 68.3(dd, J=9.0Hz, 2.5Hz) (in CDCl3) 66.6(d, J=11.3Hz) (in CDCl3) |
| 15 |  | 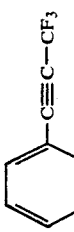 | 2 | DMF | 80° C. | 5 hours |  | 35 15 | 61.7(s) (in DMF) 59.3(s) (in DMF) |

TABLE 2-continued

| Referential Example No. | Substrate | (I) | Molar ratio substrate/(I) | Solvent | Temperature | Time | Product | Yield (%) | $^{19}$F-NMR (ppm, CFCl$_3$, internal standard) |
|---|---|---|---|---|---|---|---|---|---|
| 16 |  | 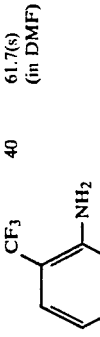 | 2 | DMF | 80° C. | 8 hours |  | 40 | 61.7(s) (in DMF) |
| | | | | | | | | 15 | 59.3(s) (in DMF) |
| 17 | 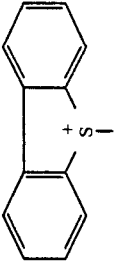 |  | 1 | DMF | 0° C. | 2 hours |  | 49 | 69.2(d, J = 8.5Hz) (in CDCl$_3$) |
| | | | | | | | | 26 | 69.75(d, J = 8Hz) (in CDCl$_3$) |
| 18 | n-C$_{12}$H$_{25}$S$^\ominus$Na$^\oplus$ | 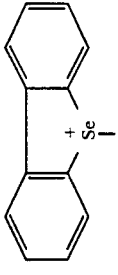 | 1 | THF | room temperature | 30 min. | n-C$_{12}$H$_{25}$SCF$_3$ | 87 | 41.5(s) (in CDCl$_3$) |
| 19 |  | 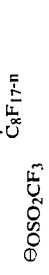 | 1 | DMF | −65° C. ⟶ room temperature | 3 hours |  | 38 | 81.3(3F, t, J = 10Hz) 112.8(2F, m) 117.4(2F, m) 122.4(6F, m) 123.4(2F, m) 126.8(2F, m) (in CDCl$_3$) |

We claim:

1. A (perfluoroalkyl)dibenzonium salt represented by the following general formula

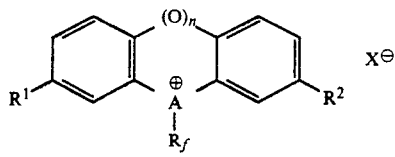
(I)

wherein $R_f$ represents a perfluoroalkyl group having 1 to 10 carbon atoms, A represents a sulfur or selenium atom, $R^1$ and $R^2$, independently from each other, represents a hydrogen atom or a nitro group, $X^\ominus$ represents a conjugated base of Brönsted acid, and n is 0 or 1.

2. The compound of claim 1 in which all of $R^1$ and $R^2$ are hydrogen atoms.

3. The compound of claim 1 in which one or both of $R^1$ and $R^2$ represent a nitro group.

4. The compound of claim 1 in which A represents a sulfur atom.

5. The compound of claim 1 in which A is a selenium atom.

6. The compound of claim 1 in which $X^\ominus$ is trifluoromethanesulfonate anion or tetrafluoroborate anion.

* * * * *